US009655727B2

(12) United States Patent
Wellings et al.

(10) Patent No.: US 9,655,727 B2
(45) Date of Patent: May 23, 2017

(54) EXTENDED PATELLOFEMORAL

(71) Applicant: Stryker Corporation, Kalamazoo, MI (US)

(72) Inventors: Peter John Wellings, Morristown, NJ (US); Michael C. Ferko, Warwick, NY (US); Stuart L. Axelson, Jr., Succasunna, NJ (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 14/104,693

(22) Filed: Dec. 12, 2013

(65) Prior Publication Data

US 2015/0164647 A1 Jun. 18, 2015

(51) Int. Cl.
*A61F 2/38* (2006.01)

(52) U.S. Cl.
CPC .......... *A61F 2/3859* (2013.01); *A61F 2/3877* (2013.01)

(58) Field of Classification Search
CPC ........ A61F 2/38; A61F 2/3877; A61F 2/3859; A61F 2002/3895; A61F 2002/30879; A61F 2002/30892
USPC ................... 623/20.15–20.21, 20.3
See application file for complete search history.

(56) References Cited

U.S. PATENT DOCUMENTS

| | | | |
|---|---|---|---|
| 3,715,763 A * | 2/1973 | Link | 623/20.3 |
| 3,774,244 A * | 11/1973 | Walker | 623/20.3 |
| 4,470,158 A * | 9/1984 | Pappas et al. | 623/20.21 |
| 5,035,699 A | 7/1991 | Coates | |
| 5,092,895 A * | 3/1992 | Albrektsson et al. | 623/20.3 |
| 5,415,662 A | 5/1995 | Ferrante et al. | |
| 5,682,886 A | 11/1997 | Delp et al. | |
| 5,702,459 A | 12/1997 | Hummer et al. | |
| 5,702,467 A | 12/1997 | Gabriel et al. | |
| 5,824,098 A | 10/1998 | Stein | |
| 5,871,018 A | 2/1999 | Delp et al. | |
| 5,880,976 A | 3/1999 | DiGioia, III et al. | |
| 6,074,425 A * | 6/2000 | Pappas | 623/18.11 |

(Continued)

OTHER PUBLICATIONS

Avon Patello-Femoral Arthroplasty, Stryker Howmedica Osteonics, date not known.

(Continued)

*Primary Examiner* — Alvin Stewart
(74) *Attorney, Agent, or Firm* — Lerner, David, Littenberg, Krumholz & Mentlik, LLP

(57) ABSTRACT

Disclosed herein are knee replacement systems for replacing the articular surface of a distal femur. The systems include one or more unicompartmental components, namely patellofemoral, lateral condylar and medial condylar components. The components are configured such that when engaged to the femur the peripheries thereof do not cross specific locations and/or regions of the femur, namely the intercondylar notch and condylopatellar notch. The patellofemoral components described herein preferably have an extension portion extending posteriorly from a posterior periphery thereof towards an intercondylar notch or the femur without contacting the intercondylar notch of the femur when the patellofemoral component is engaged to the femur. The extension portion preferably extends posteriorly from a posterior periphery of the patellofemoral component towards the condylopatellar notch of the femur without contacting the notch.

20 Claims, 7 Drawing Sheets

(56) References Cited

U.S. PATENT DOCUMENTS

| | | | |
|---|---|---|---|
| 6,132,468 A * | 10/2000 | Mansmann | 623/20.16 |
| 6,165,221 A * | 12/2000 | Schmotzer | 623/20.11 |
| 6,197,064 B1 | 3/2001 | Haines et al. | |
| 6,205,411 B1 | 3/2001 | DiGioia, III et al. | |
| 6,235,060 B1 * | 5/2001 | Kubein-Meesenburg et al. | 623/20.31 |
| 6,364,910 B1 | 4/2002 | Shultz et al. | |
| 6,423,063 B1 | 7/2002 | Bonutti | |
| 6,468,289 B1 | 10/2002 | Bonutti | |
| 6,482,209 B1 | 11/2002 | Engh et al. | |
| 6,494,914 B2 * | 12/2002 | Brown et al. | 623/20.3 |
| 6,503,267 B2 | 1/2003 | Bonutti et al. | |
| 6,503,277 B2 | 1/2003 | Bonutti | |
| 6,520,964 B2 | 2/2003 | Tallarida et al. | |
| 6,575,982 B1 | 6/2003 | Bonutti | |
| 6,589,283 B1 * | 7/2003 | Metzger et al. | 623/20.35 |
| 6,610,067 B2 | 8/2003 | Tallarida et al. | |
| 6,616,696 B1 * | 9/2003 | Merchant | 623/20.18 |
| 6,620,181 B1 | 9/2003 | Bonutti | |
| 6,635,073 B2 | 10/2003 | Bonutti | |
| 6,679,917 B2 | 1/2004 | Ek | |
| 6,702,821 B2 | 3/2004 | Bonutti | |
| 6,712,856 B1 | 3/2004 | Carignan et al. | |
| 6,723,102 B2 | 4/2004 | Johnson et al. | |
| 6,749,638 B1 * | 6/2004 | Saladino | 623/20.14 |
| 6,770,078 B2 | 8/2004 | Bonutti | |
| 6,800,094 B2 | 10/2004 | Burkinshaw | |
| 6,916,341 B2 * | 7/2005 | Rolston | 623/20.3 |
| 7,029,479 B2 | 4/2006 | Tallarida et al. | |
| 7,104,996 B2 | 9/2006 | Bonutti | |
| 7,115,131 B2 * | 10/2006 | Engh et al. | 606/79 |
| 7,163,541 B2 | 1/2007 | Ek | |
| 7,172,597 B2 * | 2/2007 | Sanford | 606/88 |
| 7,258,701 B2 * | 8/2007 | Aram | A61B 17/14 623/20.15 |
| 7,510,558 B2 | 3/2009 | Tallarida et al. | |
| 7,520,901 B2 | 4/2009 | Engh et al. | |
| 7,544,209 B2 * | 6/2009 | Lotke | 623/20.19 |
| 7,559,928 B2 | 7/2009 | Johnson et al. | |
| 7,581,118 B2 | 8/2009 | McGovern | |
| 7,582,118 B2 * | 9/2009 | Brown et al. | 623/20.36 |
| 7,604,637 B2 | 10/2009 | Johnson et al. | |
| 7,604,641 B2 | 10/2009 | Tallarida et al. | |
| 7,615,054 B1 | 11/2009 | Bonutti | |
| 7,618,451 B2 | 11/2009 | Berez et al. | |
| 7,618,462 B2 | 11/2009 | Ek | |
| 7,678,151 B2 | 3/2010 | Ek | |
| 7,695,477 B2 | 4/2010 | Creger et al. | |
| 7,713,305 B2 | 5/2010 | Ek | |
| 7,758,652 B2 | 7/2010 | Engh et al. | |
| D622,854 S | 8/2010 | Otto et al. | |
| 7,799,084 B2 * | 9/2010 | Clemow et al. | 623/20.15 |
| D625,415 S | 10/2010 | Otto et al. | |
| 7,806,898 B2 | 10/2010 | Justin et al. | |
| 7,815,645 B2 | 10/2010 | Haines | |
| 7,828,853 B2 | 11/2010 | Ek et al. | |
| 7,842,092 B2 * | 11/2010 | Otto | A61B 19/22 623/18.11 |
| 7,857,814 B2 | 12/2010 | Haines | |
| 7,857,817 B2 | 12/2010 | Tallarida et al. | |
| 7,896,883 B2 | 3/2011 | Ek et al. | |
| 7,896,885 B2 | 3/2011 | Miniaci et al. | |
| 7,896,922 B2 | 3/2011 | Engh et al. | |
| 7,896,923 B2 * | 3/2011 | Blackwell et al. | 623/20.21 |
| 7,896,924 B1 * | 3/2011 | Servidio | 623/20.3 |
| 7,901,408 B2 | 3/2011 | Ek et al. | |
| 7,914,545 B2 | 3/2011 | Ek | |
| 7,951,163 B2 | 5/2011 | Ek | |
| 7,985,225 B2 | 7/2011 | Johnson et al. | |
| 8,002,840 B2 * | 8/2011 | Aram et al. | 623/20.15 |
| 8,021,368 B2 | 9/2011 | Haines | |
| 8,128,704 B2 * | 3/2012 | Brown et al. | 623/20.15 |
| 8,157,868 B2 * | 4/2012 | Walker et al. | 623/20.32 |
| 8,216,319 B2 * | 7/2012 | Rhodes | 623/20.15 |
| 8,234,097 B2 * | 7/2012 | Steines et al. | 703/1 |
| 8,265,949 B2 | 9/2012 | Haddad | |
| 8,287,545 B2 | 10/2012 | Haines | |
| 8,317,869 B2 * | 11/2012 | Cloutier et al. | 623/20.3 |
| 8,480,754 B2 * | 7/2013 | Bojarski | A61F 2/30942 606/79 |
| 8,500,816 B2 * | 8/2013 | Dees, Jr. | A61B 17/155 623/20.14 |
| 8,535,383 B2 * | 9/2013 | Aram et al. | 623/20.15 |
| 8,545,569 B2 * | 10/2013 | Fitz et al. | 623/20.14 |
| 8,702,802 B2 * | 4/2014 | Linares et al. | 623/20.21 |
| 8,753,403 B2 * | 6/2014 | Linares et al. | 623/20.21 |
| 8,882,847 B2 * | 11/2014 | Burdulis, Jr. | A61F 2/30942 623/20.32 |
| 8,926,709 B2 * | 1/2015 | Lenz et al. | 623/23.42 |
| 2002/0068979 A1 * | 6/2002 | Brown et al. | 623/20.3 |
| 2002/0082703 A1 | 6/2002 | Repicci | 623/20.29 |
| 2002/0138150 A1 * | 9/2002 | Leclercq | 623/20.35 |
| 2003/0033018 A1 | 2/2003 | Merchant | |
| 2003/0120346 A1 * | 6/2003 | Mercinek et al. | 623/20.19 |
| 2003/0158606 A1 * | 8/2003 | Coon et al. | 623/20.15 |
| 2003/0181984 A1 | 9/2003 | Abendschein | |
| 2003/0220697 A1 * | 11/2003 | Justin et al. | 623/20.15 |
| 2003/0225458 A1 | 12/2003 | Donkers et al. | |
| 2003/0236521 A1 | 12/2003 | Brown et al. | |
| 2004/0006394 A1 * | 1/2004 | Lipman et al. | 623/20.29 |
| 2004/0102851 A1 | 5/2004 | Saladino | 623/20.15 |
| 2004/0102852 A1 | 5/2004 | Johnson et al. | 623/20.15 |
| 2004/0153087 A1 * | 8/2004 | Sanford et al. | 606/88 |
| 2004/0153162 A1 * | 8/2004 | Sanford et al. | 623/20.3 |
| 2004/0167630 A1 * | 8/2004 | Rolston | 623/20.14 |
| 2004/0204760 A1 * | 10/2004 | Fitz et al. | 623/14.12 |
| 2004/0230315 A1 | 11/2004 | Ek | |
| 2005/0043807 A1 * | 2/2005 | Wood | A61F 2/3859 623/20.14 |
| 2005/0107884 A1 * | 5/2005 | Johnson et al. | 623/20.15 |
| 2005/0137708 A1 * | 6/2005 | Clark | 623/20.15 |
| 2005/0143833 A1 | 6/2005 | Merchant | |
| 2005/0154471 A1 * | 7/2005 | Aram et al. | 623/20.15 |
| 2005/0165491 A1 * | 7/2005 | Diaz | 623/20.19 |
| 2005/0177242 A1 * | 8/2005 | Lotke | 623/20.19 |
| 2005/0267584 A1 | 12/2005 | Burdulis et al. | |
| 2005/0278034 A1 * | 12/2005 | Johnson et al. | 623/20.15 |
| 2005/0283253 A1 * | 12/2005 | Coon et al. | 623/20.35 |
| 2006/0004460 A1 * | 1/2006 | Engh | A61F 2/30724 623/20.21 |
| 2006/0009855 A1 | 1/2006 | Goble et al. | |
| 2006/0015116 A1 | 1/2006 | Haines | |
| 2006/0020343 A1 | 1/2006 | Ek | |
| 2006/0025865 A1 * | 2/2006 | Reich et al. | 623/20.35 |
| 2006/0030944 A1 | 2/2006 | Haines | |
| 2006/0058882 A1 | 3/2006 | Haines | |
| 2006/0058884 A1 * | 3/2006 | Aram et al. | 623/20.15 |
| 2006/0190086 A1 * | 8/2006 | Clemow et al. | 623/20.15 |
| 2006/0235537 A1 * | 10/2006 | Kuczynski et al. | 623/20.3 |
| 2007/0032876 A1 * | 2/2007 | Clark | 623/20.32 |
| 2007/0043444 A1 * | 2/2007 | Lester | 623/20.15 |
| 2007/0100459 A1 * | 5/2007 | Rhodes | 623/20.19 |
| 2007/0100460 A1 | 5/2007 | Rhodes | |
| 2007/0118136 A1 | 5/2007 | Ek | |
| 2007/0135926 A1 * | 6/2007 | Walker | 623/20.31 |
| 2007/0150066 A1 * | 6/2007 | McMinn | 623/20.19 |
| 2007/0173858 A1 | 7/2007 | Engh et al. | |
| 2007/0179608 A1 | 8/2007 | Ek et al. | |
| 2007/0219639 A1 * | 9/2007 | Otto et al. | 623/20.19 |
| 2007/0270973 A1 | 11/2007 | Johnson et al. | |
| 2007/0288021 A1 | 12/2007 | Rickels et al. | |
| 2008/0033443 A1 | 2/2008 | Sikora et al. | |
| 2008/0058945 A1 * | 3/2008 | Hajaj | A61F 2/38 623/20.14 |
| 2008/0058949 A1 * | 3/2008 | Dees | A61B 17/155 623/20.35 |
| 2008/0119938 A1 * | 5/2008 | Oh | 623/20.14 |
| 2008/0172125 A1 | 7/2008 | Ek | |
| 2008/0183174 A1 | 7/2008 | Sikora et al. | |
| 2008/0183177 A1 | 7/2008 | Fox et al. | |
| 2008/0188942 A1 * | 8/2008 | Brown et al. | 623/20.15 |
| 2008/0195113 A1 | 8/2008 | Sikora | |
| 2008/0195221 A1 | 8/2008 | Howald et al. | |
| 2008/0234688 A1 | 9/2008 | Johnson et al. | |

(56) References Cited

U.S. PATENT DOCUMENTS

| | | |
|---|---|---|
| 2008/0300689 A1 | 12/2008 | McKinnon et al. |
| 2009/0076514 A1 | 3/2009 | Haines |
| 2009/0082773 A1 | 3/2009 | Haines |
| 2009/0132055 A1* | 5/2009 | Ferro .................... 623/20.21 |
| 2009/0138018 A1 | 5/2009 | Haines |
| 2009/0149965 A1 | 6/2009 | Quaid |
| 2009/0192620 A1 | 7/2009 | Ebbitt |
| 2009/0228111 A1* | 9/2009 | Otto .................... A61F 2/38 623/20.19 |
| 2009/0248167 A1* | 10/2009 | Lotke .................... 623/20.19 |
| 2009/0265012 A1* | 10/2009 | Engh et al. .............. 623/20.18 |
| 2009/0270994 A1* | 10/2009 | Schaefer et al. .......... 623/20.3 |
| 2009/0281583 A1 | 11/2009 | Brown et al. |
| 2010/0070045 A1 | 3/2010 | Ek |
| 2010/0070048 A1 | 3/2010 | Tallarida et al. |
| 2010/0094429 A1 | 4/2010 | Otto |
| 2010/0125338 A1* | 5/2010 | Fitz .................... 623/20.18 |
| 2010/0145343 A1 | 6/2010 | Johnson et al. |
| 2010/0153081 A1 | 6/2010 | Bellettre et al. |
| 2010/0185294 A1 | 7/2010 | Ek |
| 2010/0191245 A1 | 7/2010 | Ek et al. |
| 2010/0204701 A1 | 8/2010 | Tallarida et al. |
| 2010/0217400 A1 | 8/2010 | Nortman et al. |
| 2010/0268238 A1 | 10/2010 | Sikora et al. |
| 2010/0268239 A1 | 10/2010 | Sikora et al. |
| 2010/0280624 A1 | 11/2010 | Engh et al. |
| 2010/0305708 A1* | 12/2010 | Lang et al. ............ 623/20.18 |
| 2010/0312342 A1 | 12/2010 | Ek |
| 2011/0015749 A1* | 1/2011 | Engh et al. ............ 623/20.15 |
| 2011/0066079 A1 | 3/2011 | Otto et al. |
| 2011/0071641 A1 | 3/2011 | Ek et al. |
| 2011/0152869 A1 | 6/2011 | Ek et al. |
| 2011/0152870 A1 | 6/2011 | Miniaci et al. |
| 2011/0196434 A1 | 8/2011 | Ek et al. |
| 2011/0213375 A1 | 9/2011 | Sikora et al. |
| 2011/0218635 A1* | 9/2011 | Amis et al. ............ 623/20.18 |
| 2011/0238074 A1 | 9/2011 | Ek |
| 2012/0089147 A1 | 4/2012 | Kuczynski |
| 2012/0109324 A1 | 5/2012 | Keggi et al. |
| 2012/0116526 A1 | 5/2012 | Forsell |
| 2012/0330429 A1* | 12/2012 | Axelson et al. .......... 623/20.19 |
| 2014/0142713 A1* | 5/2014 | Wright et al. ........... 623/20.21 |
| 2014/0358241 A1* | 12/2014 | Afriat .................. 623/20.19 |

OTHER PUBLICATIONS

Avon Patello-Femoral Arthroplasty, Surgical Protocol, Stryker, 2004.

Howmedica Surgical Techniques, Kinemax Plus Condylar Knee, Kinez Plus Stabilizer Knee, Surgical Technique, Pfizer, 1992.

Kinemax Plus Femoral Spacer with Long Stem Surgical Guide, Pfizer, 1991.

Kinemax, Howmedica Kinemax Instrument Surgical Technique, 12 pages, date not known.

Monogram, Kinemax Plus Total Knee System, Operative Texhniw Highlights, Howmedica, 1998.

Van Jonbergen, H. P. W. et al., Differences in the stress distribution in the distal femur between patellofemoral joint replacement and total knee replacement: a finite element study, Journal of Orthopaedic Surgery and Research, 2012, vol. 7, No. 1, Article No. 28 See abstract; and pp. 3-7.

International Search Report and Written Opinion for Application No. PCT/US2014/070005 dated Feb. 26, 2015.

Walker et al., "Relative positions of the contacts on the cartilage surfaces of the knee joint", The Knee, Apr. 13, 2006, pp. 382-388.

* cited by examiner

EXTENDED PATELLOFEMORAL

FIELD OF THE INVENTION

The present invention relates to patellofemoral implants and in particular relates to such implants having an extension portion designed to cover the medial and/or lateral aspect of the patellofemoral compartment posteriorly up to the intercondylar notch and condylopatellar notch.

BACKGROUND OF THE INVENTION

The knee joint includes three bones, namely the femur, tibia and patella. The distal end of the femur lies adjacent to the proximal end of the tibia while the patella lies adjacent the anterior portion of the femur. The joint elements that engage one another are preferably covered by articular cartilage. Specifically, the distal end of the femur and the proximal end of the tibia are covered by articular cartilage, as is the posterior surface of the patella.

The articular cartilage of the knee joint may become damaged due to degeneration and/or wear, which may lead to bone-to-bone contact during articulation of the joint. This may result in significant pain and potential damage to the bone surfaces. A knee replacement procedure may be required in cases where damage to the articular cartilage is significant. Depending on the extent of the damage, the procedure may include at least partial replacement of one or bone of the knee joint. For instance, in a total knee replacement each of the bones of the knee joint is at least partially covered by implants. In other instances, a knee arthroplasty procedure may be limited to portions of one of the joints. For instance, a patellofemoral procedure is limited to at least partial replacement of the engagement surfaces between the femur and the patella.

The medial and lateral condylopatellar notches represent a border between the patellofemoral and tibiofemoral articulations of the distal femur. The condylopatellar notch is a concave depression formed between the patellofemoral compartment and the medial and lateral compartments respectively. The concave depression is formed at least in part due to femoral contact with the tibial meniscus when the leg is extended. The geometry of the concave depression is in contrast to the convex geometries of the adjacent compartments. The sulcus of the condylopatellar notch forms a spline that represents a transition region or functional boarder between the compartments of the knee. This spline can be simplified to a best-fit line which substantially describes the location and trajectory of the border.

Conventional patellofemoral implants typically cover the femoral trochlea only and generally require that a lateral tibiofemoral component, for example, extend past the condylopatellar notch into the patellofemoral compartment. In the case where no lateral tibiofemoral implant is implanted, a surgeon must carefully plan the transition between the patellofemoral implant and the native cartilage. In such cases, it is expected that the patella will frequently transition from the patellofemoral component to the native condylar cartilage during active and deep flexion.

BRIEF SUMMARY OF THE INVENTION

The patellofemoral implants of the present invention improve implant coverage of each compartment of the distal femur for a larger percentage of the population. By designing the implants to only cover the region inside the condylopatellar border, anatomical variability reduces and less implant sizes and shapes are required to cover more people. Extension of the lateral flange of the implants helps to ensure that the patella remains in contact with the implants instead of stepping off the implants when transitioning to native cartilage laterally of the distal femur, medial cartilage or a medial unicompartmental implant.

A first aspect of the present invention is a patellofemoral unicompartmental implant with a posterior periphery that extends posteriorly toward the medial and/or lateral condylopatellar notch without crossing the notch. Such a patellofemoral implant may be used as a stand-alone device or in conjunction with a medial and/or lateral tibiofemoral unicompartmental implant each having an anterior periphery that extends anteriorly toward the respective medial and/or lateral condylopatellar notch without crossing the respective notch.

One embodiment of this first aspect is that the patellofemoral implant preferably replaces the articular cartilage and bone in the patellofemoral compartment. A lateral aspect of the implant is designed to cover a lateral aspect of the patellofemoral compartment posteriorly up to the condylopatellar notch and above the intercondylar notch without crossing the condylopatellar notch or contacting the intercondylar notch.

A second aspect of the present invention is a patellofemoral component for replacing at least a portion of a femur comprising a lateral portion configured to cover at least a portion of the femur, an intermediate portion adjacent to the lateral portion and configured to cover at least a portion of a length of a trochlear groove of the femur, and a medial portion adjacent to the intermediate portion and configured to cover at least a portion of the femur. The patellofemoral components include an extension portion extending posteriorly from the intermediate portion towards an intercondylar notch of the femur without contacting the intercondylar notch of the femur when the patellofemoral component is engaged to the femur.

In one embodiment of this second aspect the extension portion extends posteriorly from the lateral portion and the intermediate portion.

In another embodiment, the extension portion extends along at least a portion of a condylopatellar notch of the femur and substantially parallel to the condylopatellar notch without contacting the notch.

In yet another embodiment, the medial portion covers at least a portion of an anterior portion of a medal condyle of the femur without contacting the condylopatellar notch and the extension portion covers at least a portion of a posterior portion of a lateral condyle of the femur without contacting the condylopatellar notch.

In still yet another embodiment, the lateral portion has a first posterior periphery, the intermediate portion has a second posterior periphery, the medial portion has a third posterior periphery, and the extension portion is located at a junction between the first and second posterior peripheries. The extension portion may protrude posteriorly from the junction as a nub portion. The extention portion may protrude posteriorly from the junction along a substantial portion of the first posterior periphery.

A third aspect of the present invention is a knee replacement system for replacing at least a portion of a femur comprising a patellofemoral component including an extension portion extending posteriorly from a posterior periphery thereof towards an intercondylar notch of the femur without contacting the intercondylar notch of the femur when the patellofemoral component is engaged to the femur, and a condylar implant including a recessed portion opposed to the extension portion of the patellofemoral component when the condylar portion is engaged to a condyle of the femur, the recessed portion located adjacent the intercondylar notch of the femur without contacting the intercondylar notch.

In one embodiment of this third aspect, the patellofemoral component includes a lateral portion configured to cover at least a portion of the femur.

In another embodiment, the patellofemoral component includes an intermediate portion connected to the lateral portion configured to cover at least a portion of a length of a trochlear groove of the femur. The patellofemoral component further includes a medial portion connected to the intermediate portion configured to cover at least a portion of the femur.

In yet another embodiment, the extension portion extends posteriorly from the intermediate portion towards a condylopatellar notch of the femur without contacting the notch.

In still yet another embodiment, the lateral portion has a first posterior periphery, the intermediate portion has a second posterior periphery, the medial portion has a third posterior periphery, and the extension portion is located at a junction between the first and second posterior peripheres. The extension portion may protrude posteriorly from the junction as a nub portion. The extention portion may protrude posteriorly from, the junction along a substantial portion of the first posterior periphery.

A fourth aspect of the present invention is a knee replacement system for replacing at least a portion of a femur comprising a patellofemoral component including an extension portion configured to overlie a portion of a lateral condyle of the femur above an intercondylar notch of the femur without contacting the intercondylar notch of the femur when the patellofemoral implant is engaged to the femur, and a condylar implant including a recessed portion opposed to the extension portion of the patellofemoral component when the condylar portion is engaged to a condyle of the femur, the recessed portion located anteriorly to a condylopatellar notch of the femur.

In one embodiment of this aspect, the extension portion extends posteriorly from a posterior periphery of the patellofemoral component towards the condylopatellar notch of the femur without contacting the notch.

In another embodiment, the patellofemoral component includes a lateral portion having a first posterior periphery, an intermediate portion having a second posterior periphery, a medial portion having a third posterior periphery, and the extension portion is located at a junction between the first and second posterior peripheries. The extension portion may protrude posteriorly from the junction as a nub portion. The extention portion may protrude posteriorly from the junction along a substantial portion of the first posterior periphery.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
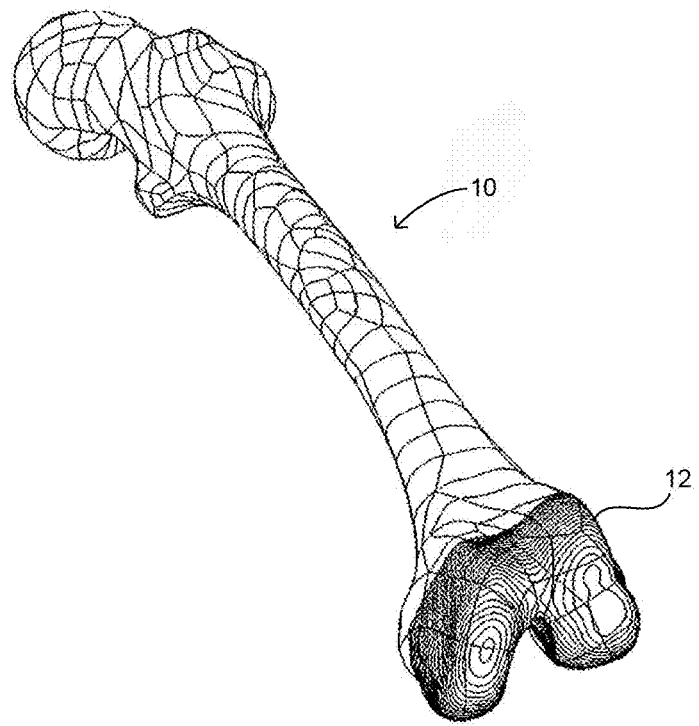
FIG. 1 is a topographic isometric view of a left femur.
Figure 2:
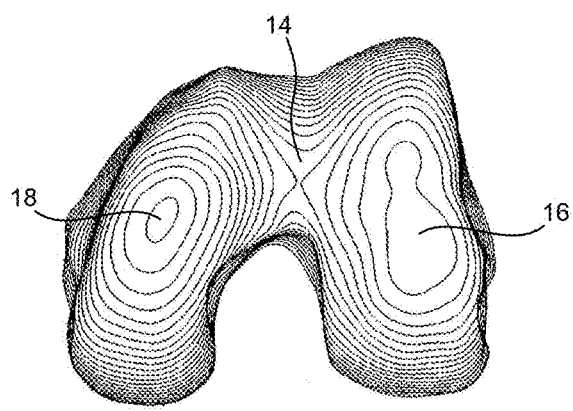
FIG. 2 is a topographic distal view of a distal end of the left femur shown in FIG. 1.

Referring to the drawings, wherein like reference numerals represent like elements, there is shown in the figures, in accordance with embodiments of the present invention, patellofemoral and condylar implants engaged to a resected distal end 12 of a femur, designated generally by reference numeral 10. FIGS. 1-2A are topographic isometric and distal views respectively of distal end 12 of femur 10 showing the contour of the outer surface thereof. As can be seen from these figures, femur 10 is a left femur having three regions, namely the trochlear groove 14, lateral condyle 16, and medial condyle 18. The topography of these areas or regions is referenced generally by the varying line curvature thereof.

Figure 3A:
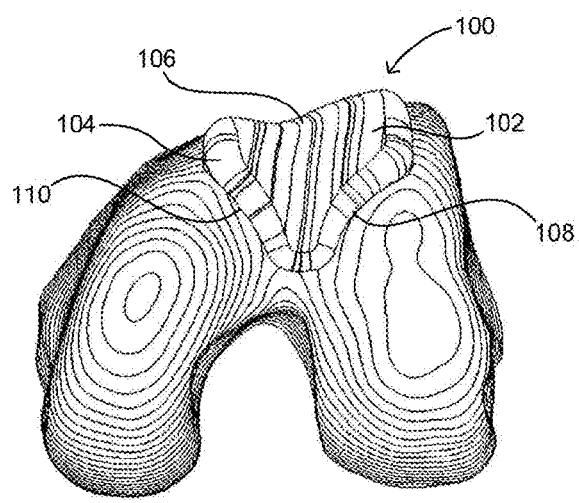
FIG. 3A is topographic distal view of a traditional patellofemoral implant engaged to the distal end of the left femur shown in FIG. 1.

FIG. 3A is topographic distal view of a traditional patellofemoral implant 100 engaged to the distal end of the left femur shown in FIG. 1. Implant 100 includes an articular surface 102 having an outer periphery 104 and a trochlear groove 106, for example. Prior to being engaged to the distal end 12 of the left femur 10 shown in FIG. 1, the distal end 12 of femur 10 may be resected either by standard or custom instrumentation, including guides and reamers, for example. Once engaged to distal end 12 of femur 10, articular surface 102 of implant 100 is generally located where the outer surface of the articular cartilage of the distal femur was located prior to any degeneration or wear thereof. Surgeon preference however may be to alter the location of articular surface 102 of implant 100 once engaged to distal end 12 of femur 10 such that it is not located exactly where the outer surface of the articular cartilage of the distal femur was located prior to any degeneration of wear thereof.

Figure 3B:
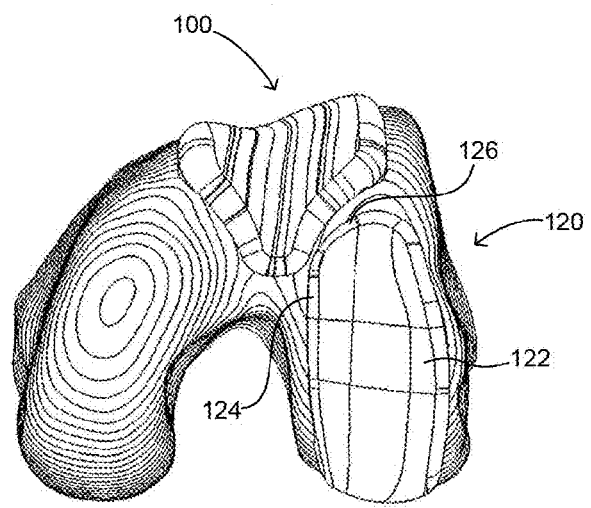
FIG. 3B is a topographic distal view of the traditional patellofemoral implant shown in FIG. 3 and a traditional lateral condylar implant each engaged to the distal end of the left femur shown in FIG. 1.
Figure 3C:
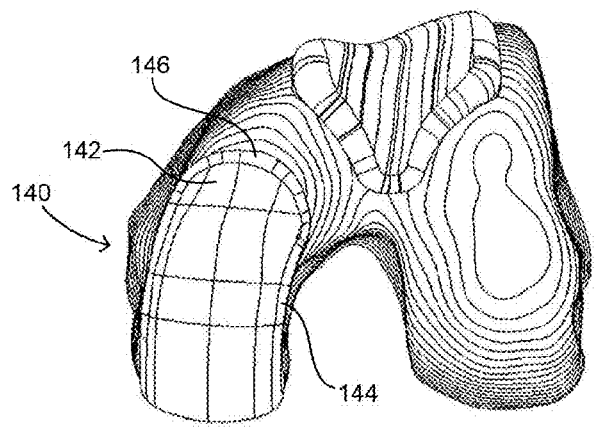
FIG. 3C is a topographic distal view of the traditional patellofemoral implant shown in FIG. 3 and a traditional medial condylar implant each engaged to the distal end of the left femur shown in FIG. 1.
Figure 4:
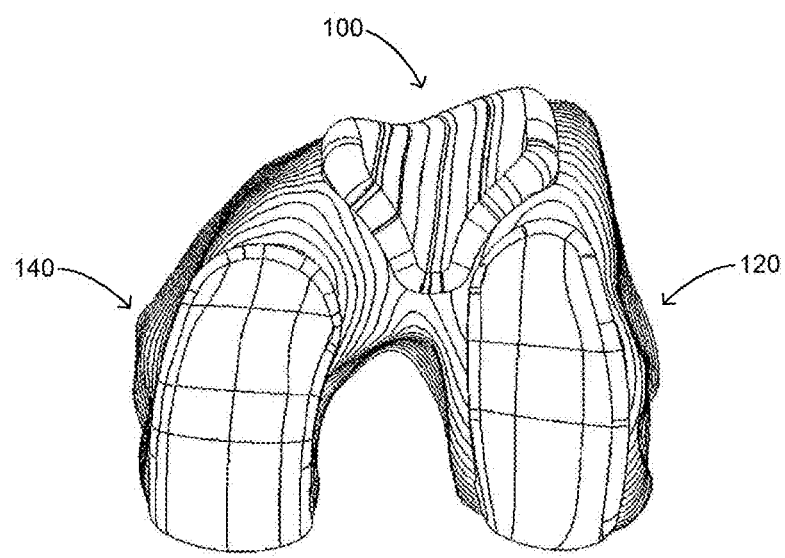
FIG. 4 is a topographic distal view of the traditional patellofemoral implant shown in FIG. 3A and traditional lateral and medial and condylar implants shown in FIGS. 3B and 3C respectively each engaged to the distal end of the left femur shown in FIG. 1.

Outer periphery 104 of implant 100 includes medial and lateral recesses 108, 110 located adjacent the medial and lateral aspect of the patellofemoral compartment and above or anterior to the condylopatellar notch line. These recesses 108, 110 provide adequate clearance for a traditional lateral condylar implant 120 and/or medial condylar implant 140 engaged to the distal end of the left femur as shown in FIGS. 3B and 3C. Each of lateral and medial condylar implants 120, 140 include articular surfaces 122, 142 and outer peripheries 124, 144, respectively. An anterior portion 126, 146 of lateral and medial condylar implants 120, 140, respectively, lie substantially adjacent to recesses 110, 108 of implant 100 respectively, as shown in FIG. 6, for example.

Figure 5:
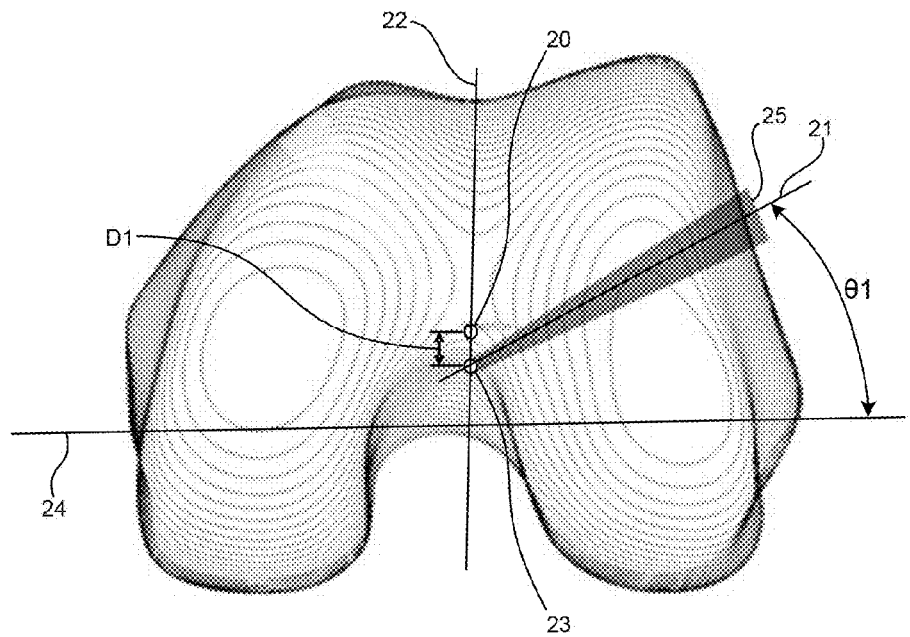
FIG. 5 is another topographic distal view of a distal end of a left femur showing the location of an intercondylar notch and a lateral condylopatellar notch line thereof.
Figure 6:
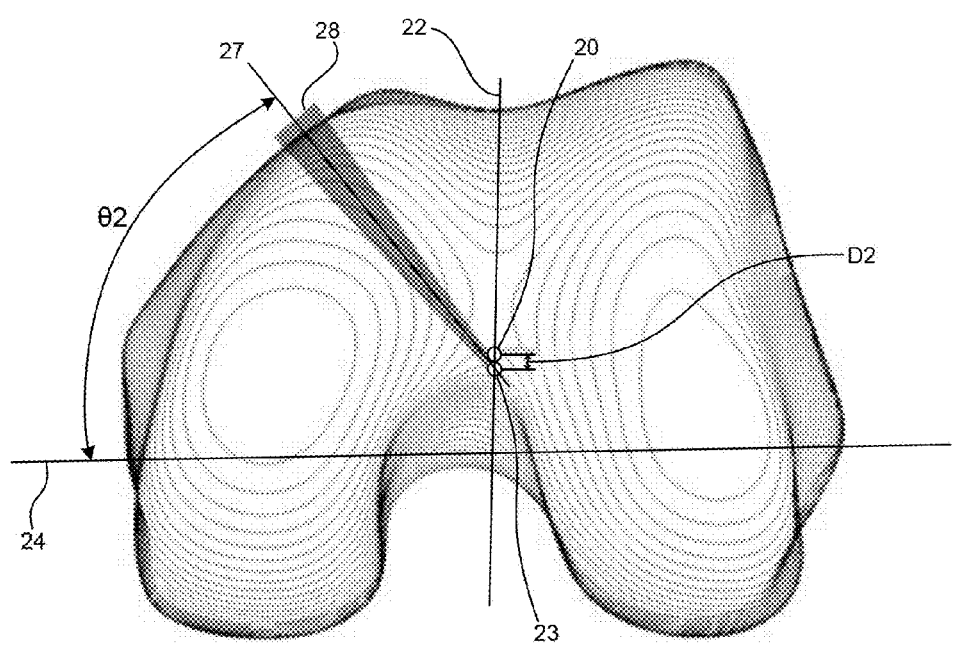
FIG. 6 is another topographic distal view of a distal end of a left femur showing the location of an intercondylar notch and a medial condylopatellar notch line thereof.

FIGS. 5 and 6 are other topographic distal views of a distal end of a left femur showing the location of an intercondylar notch 20 and lateral and medial condylopatellar notch lines 21, 27 respectively thereof. Intercondylar notch 20 is referenced as a point located in trochlear groove region 14.

As shown in FIG. 5, lateral condylopatellar notch line 21 extends across lateral condyle 16 and intersects sagittal plane 22 at intersection point 23. A posterior distance D1 is defined as the distance between intercondylar notch 20 and intersection point 23 along sagittal plane 22. An angle θ1 is the measurement of the acute internal/external rotational angle between condylopatellar notch line 21 and flexion axis 24 of the knee.

As shown in FIG. 6, medial condylopatellar notch line 27 extends across medial condyle 18 and intersects sagittal plane 22 at intersection point 23. A posterior distance D2 is defined as the distance between intercondylar notch 20 and intersection point 23 along sagittal plane 22. An angle θ2 is the measurement of the acute internal/external rotational angle between condylopatellar notch line 27 and flexion axis 24 of the knee.

A morphological analysis of 921 computed tomography ("CT") scans shows that there is a 95% likelihood that lines 21, 27 representing the lateral and medial condylopatellar notch lines, respectively, lie in boundaries 25, 28, respectively as shown in the triangular shaded regions of FIGS. 5 and 6, respectively. According to the morphological analysis, the mean posterior distance D1 is 6.4 mm with a ±1.25 mm variation as depicted by boundary 25. The mean posterior distance D2 is 2.9 mm with a ±1.20 mm variation as depicted by boundary 28. Further to the analysis, the mean angle θ1 is 22.7° with ±5.7° variation as depicted by boundary 25 and the mean angle θ2 is 47.1° with ±5.43° variation as depicted by boundary 28.

The morphological analysis described above is one method of characterizing the condylopatellar notch in one specified demographic. The three dimensional curvature of the condylopatellar notch is simplified here as being represented as a line. This analysis could be modified to represent the region as a series of arcs or a point field which may alter the shape and extents of the 95% likelihood region. This analysis could also be modified to look at specific demographics such as genders, ethnicities, and sizing measures, for example, to design implants for those groups. The analysis could be used to describe the notch over a large population to characterize a broad average shape. In any of these cases, the bounding region would then be used to define the extents of the implant extension/truncation to avoid crossing the notch. The shape of the bounding region could also be used to shape the peripheries of the implant where it approaches the notch.

Figure 7A:
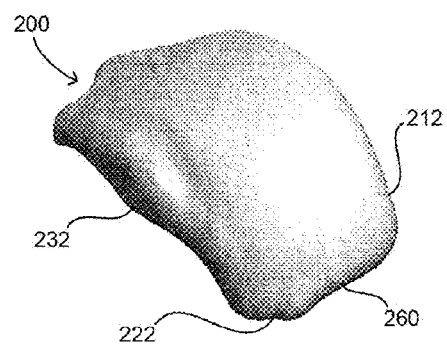
FIG. 7A is an isometric view of one embodiment of a patellofemoral implant having a first-type extension portion.
Figure 8A:
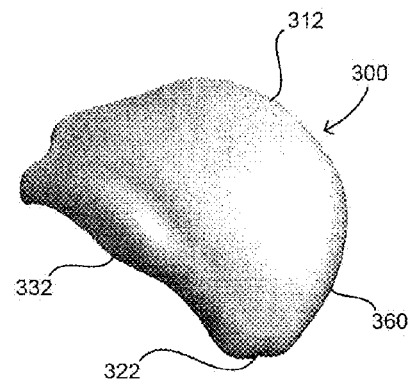
FIG. 8A is an isometric view of one embodiment of a patellofemoral implant having a second-type extension portion.
Figure 7B:
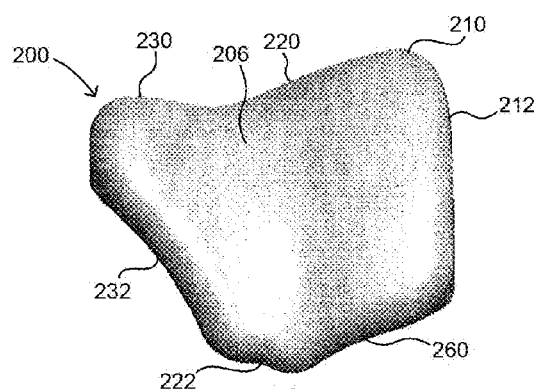
FIG. 7B is a distal view of the patellofemoral implant of FIG. 7A.
Figure 8B:
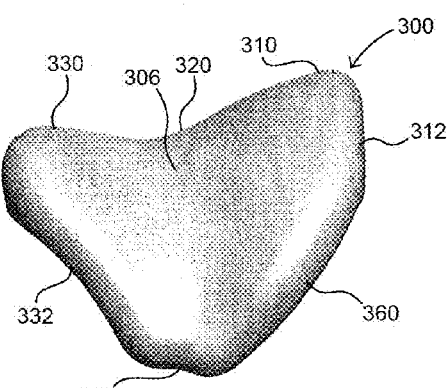
FIG. 8B is a distal view of the patellofemoral implant of FIG. 8A.
Figure 7C:
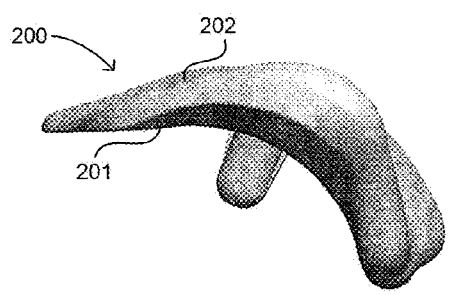
FIG. 7C is a medial view of the patellofemoral implant of FIG. 7A.
Figure 8C:
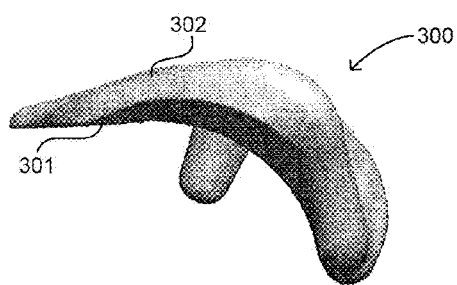
FIG. 8C is a medial view of the patellofemoral implant of FIG. 8A.

FIGS. 7A-7C show a first embodiment of a patellofemoral implant 200 having a first-type extension portion 260 and FIGS. 8A-8C show a second embodiment of a patellofemoral implant 300 having a second-type extension portion 360.

As shown in FIGS. 7A-7C, implant 200 includes a bone contacting surface 201, an articular surface 202 having an outer periphery 204 and a trochlear groove 206, for example. Implant 200 further includes a first condylar portion 210 configured to cover at least a portion of lateral condyle 16 of femur 10, an intermediate portion 220 adjacent to first condylar portion 210 configured to cover at least a portion of a length of trochlear groove 14 of femur 10, and a second condylar portion 230 adjacent to intermediate portion 220 configured to cover at least a portion of medial condyle 18 of femur 10. First condylar portion 210 has a first periphery 212, intermediate portion 220 has a second periphery 222 forming a recess and second condylar portion 230 has a third periphery 232.

Figures 9A, 9B:
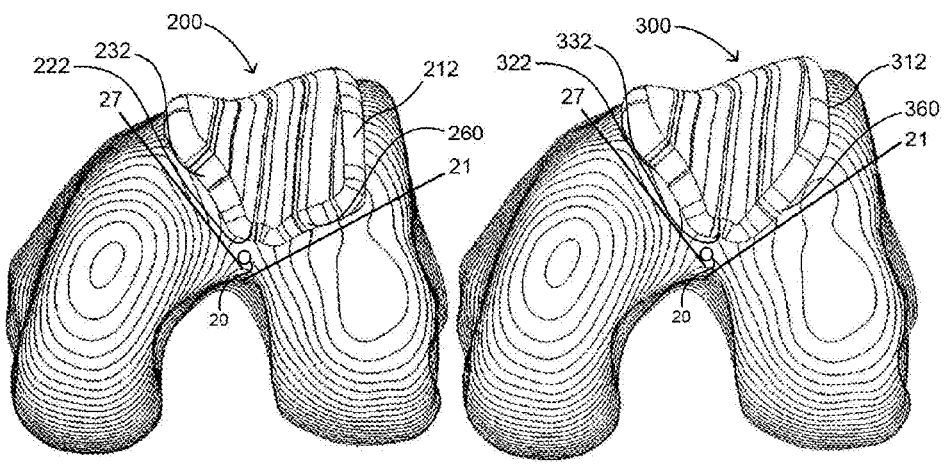
FIG. 9A is a topographic distal view of the patellofemoral implant shown in FIGS. 7A-7C each engaged to the distal end of the left femur shown in FIG. 1.
FIG. 9B is a topographic distal view of the patellofemoral implant shown in FIGS. 8A-8C each engaged to the distal end of the left femur shown in FIG. 1.

Outer periphery 204 of implant 200 differs from outer periphery 104 of implant 100 in that outer periphery 204 of implant 200 includes an extension portion 260 having a first configuration projecting posteriorly from a posterior portion thereof. Extension portion 260 is designed to cover at least a portion of a lateral aspect of the patellofemoral compartment posteriorly up to intercondylar notch 20 and condylopatellar notch line 21 of femur 10 when implant 200 is engaged to distal end 12 of femur 10 as shown in FIG. 9A. Extension portion 260 has a substantially planar periphery and is located intermediate first and second peripheries 212, 222. The periphery of extension portion 260 lies adjacent along a length of condylopatellar notch line 21 of femur 10 without crossing condylopatellar notch line 21. In this embodiment, the substantially planar periphery of extension portion 260 is substantially perpendicularly oriented to first periphery 212 of first condylar portion 210.

As shown in FIGS. 8A-8C, implant 300 includes a bone contacting surface 301, an articular surface 302 having an outer periphery 304 and a trochlear groove 306, for example. Implant 300 further includes a first condylar portion 310 configured to cover at least a portion of lateral condyle 16 of femur 10, an intermediate portion 320 adjacent to first condylar portion 310 configured to cover at least a portion of a length of trochlear groove 14 of femur 10, and a second condylar portion 330 adjacent to intermediate portion 320 configured to cover at least a portion of medial condyle 18 of femur 10. First condylar portion 310 has a first periphery 312, intermediate portion 320 has a second periphery 322 forming a recess and second condylar portion 330 has a third periphery 332.

Outer periphery 304 of implant 300 differs from outer periphery 104 of implant 100 in that outer periphery 304 of implant 300 includes an extension portion 360 having a second configuration projecting posteriorly from a posterior portion thereof. Extension portion 360 is designed to cover at least a portion of a lateral aspect of the patellofemoral compartment posteriorly up to intercondylar notch 20 and condylopatellar notch line 21 of femur 10 when implant 300 is engaged to distal end 12 of femur 10 as shown in FIG. 9B. Extension portion 360 has a substantially planar periphery and is located intermediate first and second peripheries 312, 322. The periphery of extension portion 360 lies most adjacent to condylopatellar notch line 21 of femur 10 at intermediate portion 320. In this embodiment, the substantially planar periphery of extension portion 360 is transverse to first periphery 312 of first condylar portion 310.

Figures 10A, 10B:
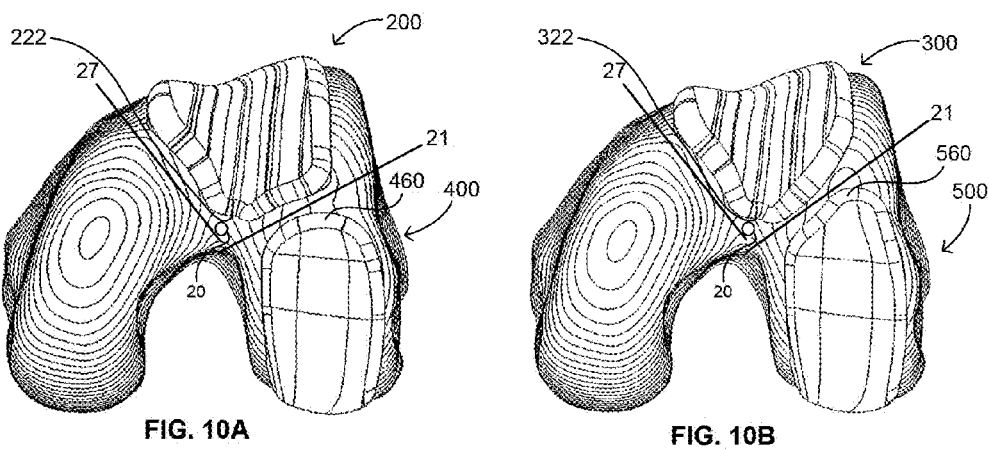
FIG. 10A is a topographic distal view of the patellofemoral implant shown in FIGS. 7A-7C and one embodiment of a first-type truncated lateral condylar implant each engaged to the distal end of the left femur shown in FIG. 1.
FIG. 10B is a topographic distal view of the patellofemoral implant shown in FIGS. 8A-8C and one embodiment of a second-type truncated lateral condylar implant each engaged to the distal end of the left femur shown in FIG. 1.

The geometry of extension portions 260, 360 of patellofemoral implants 200, 300, respectively, allows more contact with the patella through active flexion than occurs with traditional patellofemoral implants such as implant 100 shown in FIG. 3, for example. Active flexion occurs at approximately 10-110 degrees between the tibial and femoral mechanical axes with deep flexion occurring beyond 110 degrees and up to approximately 150 degrees. The geometry of extension portions 260, 360 of patellofemoral implants 200, 300, respectively, also accounts for unicondylar implants with truncated geometry to accommodate patellofemoral implants 200, 300 and to stay out of contact with patella in active flexion. Such unicondylar implants 400, 500 with truncated geometry are shown in FIGS. 10A and 10B, respectively.

Figures 11A, 11B:
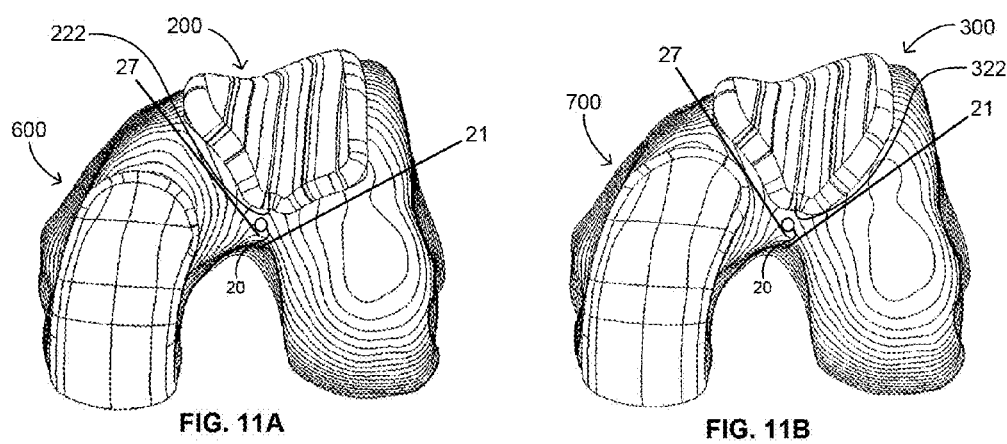
FIG. 11A is a topographic distal view of the patellofemoral implant shown in FIGS. 7A-7C and one embodiment of a medial condylar implant each engaged to the distal end of the left femur shown in FIG. 1.
FIG. 11B is a topographic distal view of the patellofemoral implant shown in FIGS. 8A-8C and one embodiment of a medial condylar implant each engaged to the distal end of the left femur shown in FIG. 1.
Figure 12A:
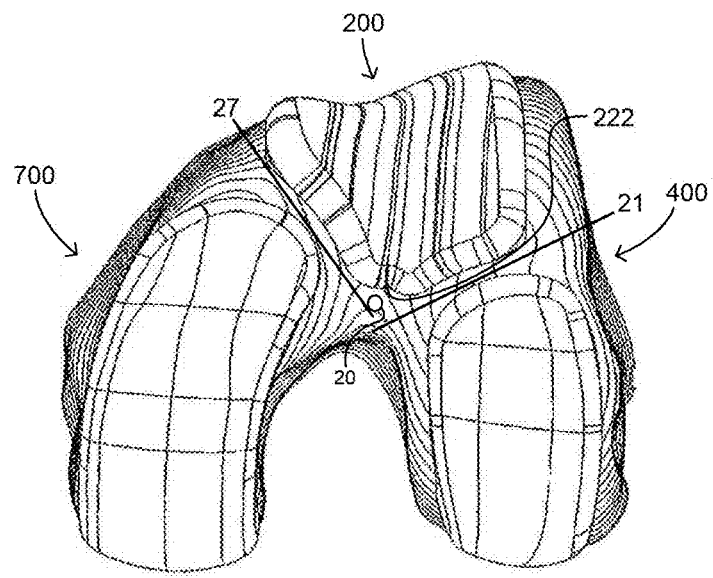
FIG. 12A is a topographic distal view of the patellofemoral implant shown in FIGS. 7A-7C, the first-type truncated lateral condylar implant shown in FIG. 10A, and the medial condylar implant shown in FIGS. 11A-11B each engaged to the distal end of the left femur shown in FIG. 1.
Figure 12B:
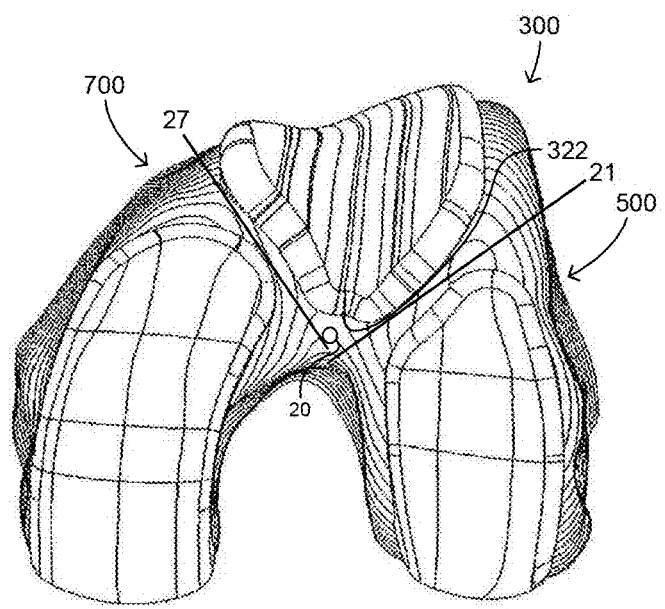
FIG. 12B is a topographic distal view of the patellofemoral implant shown in FIGS. 8A-8C, the second-type truncated lateral condylar implant shown in FIG. 10B, and the medial condylar implant shown in FIGS. 11A-11B each engaged to the distal end of the left femur shown in FIG. 1.

FIGS. 11A and 11B show patellofemoral implants 200, 300 and medial condylar implants 600, 700 respectively each engaged to distal end 12 of femur 10. FIGS. 12A and 12B show patellofemoral implants 200, 300, truncated unicondylar implants 400, 500 and medial condylar implants 700 respectively each engaged to distal end 12 of femur 10.

Without extension portions 260, 360 on patellofemoral implants 200, 300 the patella will frequently transition off and on patellofemoral implants 200, 300 during active flexion increasing the likelihood of failure if implantation is not ideal and implant materials are not well matched. A traditional patellofemoral implant such as implant 100 does not allow a lateral tibiofemoral implant such as implant 120 to be truncated without increasing the distance over which the patella must articulate with native cartilage, for example. While an extended lateral tibiofemoral component may be thought of as a solution to this problem, such an implant can be challenging to fit on many patients due to the relative variability of the peripheries of the patellofemoral and tibiofemoral compartments on either side of the condylopatellar notch 16 of a patient. Extended patellofemoral implants 200, 300 increases the length of contact with the patella during active flexion and indirectly decreases the variability of the periphery required to be covered in both the patellofemoral and tibiofemoral compartments.

The extension portion or posterior lateral periphery 260, 360 of extended patellofemoral implants 200, 300, respectively, is therefore extended to lie adjacent to condylopatellar notch line without crossing the condylopatellar notch line 21. The anterior peripheries 460, 560 of the matched lateral tibiofemoral implants 400, 500, respectively, can then be truncated to remain posterior of the condylopatellar notch 16 as shown in FIGS. 10A and 10B.

Extending the posterior lateral periphery 260, 360 of patellofemoral implants 200, 300, respectively towards condylopatellar notch line 21 allows for a number of advantages. The extended articular surfaces allow a patellar implant to remain in contact with the patellofemoral implant for a greater range of active knee flexion. This increased contact length reduces the likelihood and frequency of patella transition off the patellofemoral implant.

In a medial and patellofemoral bicompartmental knee arthroplasty case, for example, this preferably reduces the likelihood of a patellar implant from coming in contact with native cartilage. Decreased contact between native cartilage and patellar implant articular bearing materials reduces the likelihood of unfavorable material interactions with native cartilage. In a tricompartmental case or a lateral and patellofemoral bicompartmental case, for example, the increased patellofemoral contact length would reduce the frequency and likelihood of patellar transition from the patellofemoral implant to the lateral tibiofemoral implant. The reduction in the number of transitions from implant to implant preferably aid in increasing the life of the implant.

By keeping the patellofemoral implant and lateral tibiofemoral implant on either side of the condylopatellar notch line, the potential variability of the implant periphery relative to patient's periphery is reduced. When either periphery of the patellofemoral or later tibiofemoral implant is required to cross this border on a patient, that implant is required to cover the periphery of its own compartment as well as the periphery of the adjacent compartment.

It is assumed that the relative positions of these compartments are uncorrelated as they were forged by their respective articular pair. With uncorrelated relative compartment positions, the periphery across the border can be assumed to be highly variable from patient to patient. Therefore the extension of the patellofemoral implant and truncation of the lateral tibiofemoral implant allow for a reduction in the variability of the patient peripheries they are required to cover.

The extended patellofemoral implants 200, 300 and their matched truncated lateral tibiofemoral implant 400, 500 can be implanted conventionally or using robotic surgical assistance. Preoperative planning may be used as identification of the intercondylar notch and condylopatellar notch line and determining implant size and position relative to these locations may require computational analysis. Conventional implantation could be similar to the Avon patellofemoral implant manufactured by Stryker Orthopaedics, for example. Robotic implantation would consist of preoperative planning, machining of patellofemoral compartment, implantation, trial reduction and cementation (if necessary). The posterior periphery of the extended patellofemoral implants 200, 300 may be an inlay preparation, flush with the native cartilage, for example. The anterior periphery could be an onlay preparation, proud of the resected bone, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

The invention claimed is:

1. A patellofemoral component for replacing at least a portion of a femur having a sagittal plane and a lateral condylopatellar notch line transverse to the sagittal plane comprising:
   a lateral portion configured to cover at least a lateral portion of the femur;
   an intermediate portion adjacent to the lateral portion and configured to cover at least a portion of a length of a trochlear groove of the femur, the intermediate portion having a recess about a periphery thereof;
   a medial portion adjacent to the intermediate portion and configured to cover at least a medial portion of the femur, the medial portion lying adjacent both an intercondylar notch and a medial condylopatellar notch line of the femur without contacting either of the intercondylar notch or the medial condylopatellar notch line when the patellofemoral component is engaged to the femur; and
   an extension portion extending posteriorly from the recess of the intermediate portion and along the lateral portion towards the intercondylar notch and the lateral condylopatellar notch line of the femur, the recess being located on the sagittal plane and a plane defined by the extension portion intersecting the sagittal plane at a point posterior to the intercondylar notch,
   wherein the extension portion extending posteriorly from the intermediate portion is substantially planar and lies adjacent both the intercondylar notch and lateral condylopatellar notch line and extends substantially parallel to the lateral condylopatellar notch line without contacting either of the intercondylar notch or lateral condylopatellar notch line of the femur when the patellofemoral component is engaged to the femur.

2. The patellofemoral component of claim 1, wherein a portion of the extension portion extends away from at least a portion of the lateral condylopatellar notch line of the femur without contacting the condylopatellar notch line.

3. The patellofemoral component of claim 1, wherein the medial portion covers at least a portion of an anterior portion of a medial condyle of the femur without contacting the medial condylopatellar notch line.

4. The patellofemoral component of claim 1, wherein the extension portion covers at least a portion of a posterior portion of a lateral condyle of the femur without contacting the lateral condylopatellar notch line.

5. The patellofemoral component of claim 1, wherein the lateral portion has a first posterior periphery, the intermediate portion has a second posterior periphery, the medial portion has a third posterior periphery, and the extension portion is at least partially located at a junction between the first and second posterior peripheries.

6. The patellofemoral component of claim 5, wherein the extension portion protrudes posteriorly from the junction as a nub portion.

7. The patellofemoral component of claim 5, wherein the extension portion protrudes posteriorly along a substantial portion of the first posterior periphery.

8. The patellofemoral component of claim 1, wherein the extension portion lies about a line approximately 23° from a flexion axis of the femur, the flexion axis lying perpendicular to the sagittal plane.

9. The patellofemoral component of claim 1, wherein the extension portion lies about a line approximately 47° from a flexion axis of the femur, the flexion axis lying perpendicular to the sagittal plane.

10. A knee replacement system for replacing at least a portion of a femur having a sagittal plane and medial and lateral condylopatellar notch lines transverse to the sagittal plane comprising:
    a patellofemoral component including an extension portion extending posteriorly from a recess about a periphery of an intermediate portion and along a medial portion thereof towards an intercondylar notch and the medial condylopatellar notch line of the femur, the extension portion extending posteriorly from the recess of the intermediate portion being substantially planar and lying adjacent both the intercondylar notch and medial condylopatellar notch line and extending substantially parallel to the medial condylopatellar notch line without contacting either of the intercondylar notch or the medial condylopatellar notch line of the femur when the patellofemoral component is engaged to the femur, the patellofemoral component further including a lateral portion adjacent to the intermediate portion and configured to cover at least a lateral portion of the femur, the lateral portion lying adjacent both the intercondylar notch and the lateral condylopatellar notch line without contacting either of the intercondylar notch or the lateral condylopatellar notch line of the femur when the patellofemoral component is engaged to the femur; and
    a condylar implant including a recessed portion opposed to the extension portion of the patellofemoral component when the condylar portion is engaged to a condyle of the femur, the recessed portion located adjacent the intercondylar notch of the femur without contacting the intercondylar notch.

11. The knee replacement system of claim 10, wherein the intermediate portion connected to the lateral portion is configured to cover at least a portion of a length of a trochlear groove of the femur.

12. The knee replacement system of claim 11, wherein the medial portion connected to the intermediate portion is configured to cover at least a medial portion of the femur.

13. The knee replacement system of claim 11, wherein the lateral portion has a first posterior periphery, the intermediate portion has a second posterior periphery, the medial portion has a third posterior periphery, and the extension portion is located at a junction between the first and second posterior peripheries.

14. The knee replacement system of claim 13, wherein the extension portion protrudes posteriorly from the junction as a nub portion.

15. The knee replacement system of claim 13, wherein the extension portion protrudes posteriorly from the junction along a substantial portion of the first posterior periphery.

16. A knee replacement system for replacing at least a portion of a femur having a sagittal plane and medial and lateral condylopatellar notch lines transverse to the sagittal plane comprising:
    a patellofemoral component including an extension portion extending posteriorly from a recess about a periphery of an intermediate portion and along a lateral portion and configured to overlie a portion of a lateral condyle of the femur above an intercondylar notch and the lateral condylopatellar notch line of the femur, the extension portion extending posteriorly from the recess of the intermediate portion being substantially planar and lying adjacent both the intercondylar notch and lateral condylopatellar notch line and extending substantially parallel to the lateral condylopatellar notch line without contacting either of the intercondylar notch or the lateral condylopatellar notch line of the femur when the patellofemoral implant is engaged to the femur, the patellofemoral component further including a medial portion adjacent to the intermediate portion and configured to cover at least a medial portion of the femur, the medial portion lying adjacent both the intercondylar notch and the medial condylopatellar notch line without contacting either of the intercondylar notch or the medial condylopatellar notch line of the femur when the patellofemoral component is engaged to the femur; and a condylar implant including a recessed portion opposed to the extension portion of the patellofemoral component when the condylar portion is engaged to a condyle of the femur, the recessed portion located anteriorly to the lateral condylopatellar notch line of the femur.

17. The knee replacement system of claim 16, wherein the extension portion extends posteriorly from a posterior periphery of the patellofemoral component towards the lateral condylopatellar notch line of the femur without contacting the lateral condylopatellar notch line.

18. The knee replacement system of claim 16, wherein the lateral portion has a first posterior periphery, the intermediate portion has a second posterior periphery, a medial portion has a third posterior periphery, and the extension portion is located at a junction between the first and second posterior peripheries.

19. The knee replacement system of claim 18, wherein the extension portion protrudes posteriorly from the junction as a nub portion.

20. The knee replacement system of claim 18, wherein the extension portion protrudes posteriorly from the junction along a substantial portion of the first posterior periphery.

* * * * *